United States Patent
Devgon

(10) Patent No.: US 10,064,576 B2
(45) Date of Patent: Sep. 4, 2018

(54) SYSTEMS AND METHODS FOR PHLEBOTOMY THROUGH A PERIPHERAL IV CATHETER

(71) Applicant: Velano Vascular, Inc., Philadelphia, PA (US)

(72) Inventor: Pitamber Devgon, Philadelphia, PA (US)

(73) Assignee: VELANO VASCULAR, INC., San Francisco, CA (US)

( * ) Notice: Subject to any disclaimer, the term of this patent is extended or adjusted under 35 U.S.C. 154(b) by 354 days.

(21) Appl. No.: 14/933,403

(22) Filed: Nov. 5, 2015

(65) Prior Publication Data

US 2016/0051174 A1 Feb. 25, 2016

Related U.S. Application Data

(63) Continuation of application No. 13/234,857, filed on Sep. 16, 2011, now Pat. No. 9,186,100.

(60) Provisional application No. 61/479,223, filed on Apr. 26, 2011.

(51) Int. Cl.
| | |
|---|---|
| *A61B 5/15* | (2006.01) |
| *A61B 3/15* | (2006.01) |
| *A61B 5/154* | (2006.01) |
| *A61B 5/155* | (2006.01) |

(Continued)

(52) U.S. Cl.
CPC ...... *A61B 5/150992* (2013.01); *A61B 5/1427* (2013.01); *A61B 5/1438* (2013.01); *A61B 5/15003* (2013.01); *A61B 5/154* (2013.01); *A61B 5/150221* (2013.01); *A61B 5/150396* (2013.01); *A61B 5/150503* (2013.01); *A61B 5/150572* (2013.01); *A61B 5/150717* (2013.01); *A61B 5/150732* (2013.01);
(Continued)

(58) Field of Classification Search
CPC ............ A61B 5/150992; A61B 5/1427; A61B 5/1438; A61B 5/15003; A61B 5/150221
See application file for complete search history.

(56) References Cited

U.S. PATENT DOCUMENTS

| | | |
|---|---|---|
| 4,192,319 A | 3/1980 | Hargens et al. |
| 4,314,555 A | 2/1982 | Sagae |
| 4,790,830 A | 12/1988 | Hamacher |

(Continued)

FOREIGN PATENT DOCUMENTS

| | | |
|---|---|---|
| EP | 2504054 | 9/2013 |
| JP | S55-119739 U | 8/1980 |

(Continued)

OTHER PUBLICATIONS

International Search Report and Written Opinion for International Application No. PCT/US2015/046863, dated Dec. 21, 2015.

(Continued)

*Primary Examiner* — Sean Dougherty
(74) *Attorney, Agent, or Firm* — Cooley LLP

(57) ABSTRACT

An apparatus for performing phlebotomy through a peripheral intravenous line. The apparatus includes an introducer and a catheter configured to advance the catheter through a peripheral intravenous line. A y-adapter with a port of larger diameter is configured to receive the catheter and place in fluid communication with the peripheral intravenous line. When advanced the catheter is configured to transport a bodily fluid (i.e. blood) to a volume outside of the body.

20 Claims, 7 Drawing Sheets

(51) Int. Cl.
  *A61B 17/34* (2006.01)
  *A61M 39/02* (2006.01)
(52) U.S. Cl.
  CPC . *A61B 17/3415* (2013.01); *A61M 2039/0202* (2013.01); *F04C 2270/0421* (2013.01)

(56) References Cited

U.S. PATENT DOCUMENTS

| | | |
|---|---|---|
| 4,808,158 A | 2/1989 | Kreuzer et al. |
| 4,808,165 A | 2/1989 | Carr |
| 4,935,010 A | 6/1990 | Cox et al. |
| 5,013,304 A | 5/1991 | Russell et al. |
| 5,100,390 A | 3/1992 | Lubeck et al. |
| 5,135,502 A | 8/1992 | Koenig, Jr. et al. |
| 5,147,334 A | 9/1992 | Moss |
| 5,201,722 A | 4/1993 | Moorehead et al. |
| 5,203,771 A | 8/1993 | Melker et al. |
| 5,270,003 A | 12/1993 | Bernes et al. |
| 5,360,407 A | 11/1994 | Leonard |
| 5,368,029 A | 11/1994 | Holcombe et al. |
| 5,552,118 A | 9/1996 | Mayer |
| 5,553,625 A | 9/1996 | Rao |
| 5,562,631 A | 10/1996 | Bogert |
| 5,611,782 A | 3/1997 | Haedt |
| 5,658,263 A | 8/1997 | Dang et al. |
| D384,741 S | 10/1997 | Musgrave et al. |
| 5,749,857 A | 5/1998 | Cuppy |
| 5,755,709 A | 5/1998 | Cuppy |
| 5,827,229 A | 10/1998 | Auth et al. |
| 5,848,996 A | 12/1998 | Eldor |
| 5,853,393 A | 12/1998 | Bogert |
| 5,897,537 A | 4/1999 | Berg et al. |
| 5,911,715 A | 6/1999 | Berg et al. |
| 5,944,695 A | 8/1999 | Johnson et al. |
| 6,036,677 A | 3/2000 | Javier et al. |
| 6,080,138 A | 6/2000 | Lemke et al. |
| 6,093,177 A | 7/2000 | Javier et al. |
| 6,126,618 A | 10/2000 | Bischof |
| 6,197,001 B1 | 3/2001 | Wilson et al. |
| 6,508,790 B1 | 1/2003 | Lawrence |
| 6,585,703 B1 | 7/2003 | Kassel et al. |
| 6,648,835 B1 | 11/2003 | Shemesh |
| 6,652,507 B2 | 11/2003 | Pepin |
| 6,685,664 B2 | 2/2004 | Levin et al. |
| 6,692,473 B2 | 2/2004 | St Cyr et al. |
| 6,712,790 B1 | 3/2004 | Prestidge et al. |
| 6,719,726 B2 | 4/2004 | Meng et al. |
| 6,719,781 B1 | 4/2004 | Kim |
| 6,722,370 B1 | 4/2004 | Mann |
| 6,755,812 B2 | 6/2004 | Peterson et al. |
| 6,858,024 B1 | 2/2005 | Berg et al. |
| 6,908,459 B2 | 6/2005 | Harding et al. |
| 7,135,008 B2 | 11/2006 | O'Mahony et al. |
| 7,252,654 B2 | 8/2007 | VanTassel et al. |
| 7,311,689 B2 | 12/2007 | Levin et al. |
| 7,316,678 B2 | 1/2008 | Nash et al. |
| 7,462,161 B2 | 12/2008 | O'Mahony et al. |
| 7,615,033 B2 | 11/2009 | Leong |
| 7,625,367 B2 | 12/2009 | Adams et al. |
| 7,670,320 B2 | 3/2010 | Iwase et al. |
| 7,685,367 B2 | 3/2010 | Ruia et al. |
| 7,691,088 B2 | 4/2010 | Howell |
| 7,713,250 B2 | 5/2010 | Harding et al. |
| 7,717,882 B2 | 5/2010 | Harding |
| 7,717,899 B2 | 5/2010 | Bowe et al. |
| 7,762,977 B2 | 7/2010 | Porter et al. |
| 7,766,961 B2 | 8/2010 | Patel et al. |
| 7,771,394 B2 | 8/2010 | Shue et al. |
| 7,972,294 B2 | 7/2011 | Nash et al. |
| 8,062,226 B2 | 11/2011 | Moore |
| 8,092,374 B2 | 1/2012 | Smith et al. |
| 8,114,057 B2 | 2/2012 | Gerdts et al. |
| 8,251,978 B2 | 8/2012 | Nash et al. |
| 8,361,013 B2 | 1/2013 | Wood |
| 8,361,014 B2 | 1/2013 | Wood |
| 8,366,685 B2 | 2/2013 | Devgon |
| 8,372,032 B2 | 2/2013 | Wood |
| 8,425,532 B2 | 4/2013 | Flom et al. |
| 8,444,605 B2 | 5/2013 | Kuracina et al. |
| 8,491,568 B2 | 7/2013 | Schertiger et al. |
| 8,523,801 B2 | 9/2013 | Nash et al. |
| 8,696,639 B2 | 4/2014 | Smith et al. |
| 8,721,546 B2 | 5/2014 | Belson |
| 8,728,035 B2 | 5/2014 | Warring et al. |
| 8,728,058 B2 | 5/2014 | Schertiger |
| 8,753,312 B2 | 6/2014 | Bowe et al. |
| 8,808,246 B2 | 8/2014 | Cabot |
| 9,744,344 B1 | 8/2017 | Devgon et al. |
| 9,750,446 B2 | 9/2017 | Devgon et al. |
| 2002/0120215 A1 | 8/2002 | Crawford et al. |
| 2003/0083620 A1 | 5/2003 | Luther et al. |
| 2004/0092879 A1 | 5/2004 | Kraus et al. |
| 2004/0138622 A1 | 7/2004 | Palasis |
| 2004/0181192 A1 | 9/2004 | Cuppy |
| 2005/0015048 A1 | 1/2005 | Chiu et al. |
| 2005/0119597 A1 | 6/2005 | O'Mahony et al. |
| 2005/0165355 A1 | 7/2005 | Fitzgerald |
| 2005/0192558 A1 | 9/2005 | Bernard et al. |
| 2006/0015068 A1 | 1/2006 | Amisar et al. |
| 2007/0088279 A1 | 4/2007 | Shue et al. |
| 2007/0219460 A1 | 9/2007 | Goldenberg |
| 2007/0282280 A1 | 12/2007 | Tennican |
| 2008/0033396 A1 | 2/2008 | Danek et al. |
| 2008/0045862 A1 | 2/2008 | Dalebout et al. |
| 2008/0287918 A1 | 11/2008 | Rosenman et al. |
| 2008/0300574 A1 | 12/2008 | Belson et al. |
| 2008/0319387 A1 | 12/2008 | Amisar et al. |
| 2009/0156963 A1 | 6/2009 | Noble et al. |
| 2010/0210934 A1 | 8/2010 | Belson |
| 2010/0286657 A1 | 11/2010 | Heck |
| 2010/0305519 A1 | 12/2010 | McKennon et al. |
| 2011/0015577 A1 | 1/2011 | Baney et al. |
| 2012/0041392 A1 | 2/2012 | Donawick |
| 2012/0046648 A1 | 2/2012 | Scheckel |
| 2012/0053523 A1 | 3/2012 | Harding |
| 2012/0109079 A1 | 5/2012 | Asleson et al. |
| 2012/0191010 A1 | 7/2012 | Cabot |
| 2012/0277630 A1 | 11/2012 | Devgon |
| 2013/0289537 A1 | 10/2013 | Schertiger et al. |
| 2014/0012085 A1 | 1/2014 | Smith et al. |
| 2014/0046214 A1 | 2/2014 | Devgon |
| 2014/0107800 A1 | 4/2014 | Flom et al. |
| 2014/0128774 A1 | 5/2014 | Andreae et al. |
| 2014/0128775 A1 | 5/2014 | Andreae et al. |
| 2014/0171803 A1 | 6/2014 | Van Hoven et al. |
| 2014/0180127 A1 | 6/2014 | Meyer et al. |
| 2014/0188003 A1 | 7/2014 | Belson |
| 2014/0296745 A1 | 10/2014 | Cash |
| 2014/0364766 A1 | 12/2014 | Devgon |
| 2014/0378867 A1 | 12/2014 | Belson |
| 2015/0313526 A1 | 11/2015 | Van Wieren |
| 2016/0220786 A1 | 8/2016 | Mitchell et al. |
| 2016/0220790 A1 | 8/2016 | Borowicz |
| 2017/0216564 A1 | 8/2017 | Devgon et al. |

FOREIGN PATENT DOCUMENTS

| | | |
|---|---|---|
| JP | 2007-029732 A | 2/2007 |
| WO | WO 1996/021393 | 7/1996 |
| WO | WO 2000/041617 | 7/2000 |
| WO | WO 2000/049939 | 8/2000 |
| WO | WO 2006/090637 | 8/2006 |
| WO | WO 2008/097949 | 8/2008 |
| WO | WO 2008/130077 | 10/2008 |
| WO | WO 2008/138351 | 11/2008 |
| WO | WO 2010/089154 | 8/2010 |
| WO | WO 2011/011436 | 1/2011 |
| WO | WO 2011/030282 | 3/2011 |
| WO | WO 2012/149109 | 11/2012 |
| WO | WO 2013/174381 | 11/2013 |
| WO | WO 2014/093472 | 6/2014 |
| WO | WO 2016/033143 | 3/2016 |

(56) References Cited

FOREIGN PATENT DOCUMENTS

OTHER PUBLICATIONS

International Search Report and Written Opinion for International Application No. PCT/US2017/016359, dated Jun. 26, 2017, 13 pages.
International Search Report and Written Opinion from International Application No. PCT/US2010/042635, dated Feb. 25, 2011.
Notice of Preliminary Rejection for Korean Patent Application No. 10-2013-7030879, dated Feb. 6, 2018, 11 pages.
Office Action Japanese Patent Application No. 2017-038135, dated Feb. 14, 2018, 5 pages.
Office Action for Japanese Patent Application No. 2014-508539, dated Feb. 26, 2016, 4 pgs.
Office Action for Japanese Patent Application No. 2014-508539, dated Nov. 1, 2016, 6 pgs.
Office Action for Russian Patent Application No. 2013152251, dated Feb. 24, 2016, 6 pgs.
Office Action for U.S. Appl. No. 13/758,585, dated May 16, 2016, 8 pages.
Office Action for U.S. Appl. No. 14/468,826, dated Oct. 26, 2017, 7 pages.
Office Action for U.S. Appl. No. 15/199,290, dated Dec. 7, 2016, 30 pgs.
Office Action for U.S. Appl. No. 13/456,900, dated Sep. 5, 2012.
Himberger Jr., "Accuracy of drawing blood through infusing intravenous lines," 2001 [retrieved on Mar. 16, 2011] Retrieved from the Internet <URL: <http://www.ncbi.nlm.nih.gov/pubmed/?term=Accuracy%20of%20drawing%20blood%20through%20infusing%20intravenous%20lines.
Cox, et al. "Blood Samples Drawn from IV Catheters Have Less Hemolysis When 5-mL (vs 10-mL) Collection Tubes Are Used," 2004 [retrieved on Mar. 16, 2011] Retrieved from the Internet <URL: http://www.jenonline.org/article/S0099-1767(04)00634-8/fulltext>, 2 pgs.
Jagger, et al., "Drawing Venous Blood With Syringes: A Risky Use of Injection Equipment," Advances in Exposure Prevention, vol. 5, No. 3, 2000, 3 pgs.
WHO guidelines on drawing blood: best practices in phlebotomy, © World Health Organization 2010, 125 pgs.
"Connect and Protect with BD Diagnostics—Preanalytical Systems," BD Vacutainer®, Luer-Lok™, Access Device, 2 pgs.
"Needleless IV Access Devices," BD Q-Syte™, Luer Access Split-Septum, 2007, 1 pg.
"Evidence-Based Practice (EBP) Guideline Drawing Labs from Peripheral IV Sites," Nursing Research Council of United Hospital—Developed Apr. 2004; Revised Mar. 2009, 3 pgs.
Frey, "Drawing Blood Samples From Vascular Access Devices: Evidence-based Practice," Journal of Infusion Nursing: Sep./Oct. 2003, vol. 26, Issue 5, pp. 285-293, Article: CE, Abstract, [retrieved on Mar. 16, 2011], 1 pg.
"Blood Sampling Hemolysis Study for the MaxPlus™ Positive Flow Connector," Maximus Medical Products, Inc. © 2003, 1 pg.
"Vascular Access Procedures," Vascular Access Procedures, [retrieved on Mar. 16, 2011] Retrieved from the Internet <URL: http://www.radiologyinfo.org/en/info.cfm?pg=vasc_access> 7 pgs.
Office Action for U.S. Appl. No. 13/456,900, dated Nov. 2, 2012.
International Search Report and Written Opinion for International Application No. PCT/US12/35122, dated Feb. 14, 2014.
Supplementary European Search Report for European Application No. EP 12776089.0, dated May 13, 2015, 7 pgs.
Office Action for Chinese Patent Application No. 201280029672.2, dated May 26, 2015, 21 pgs.
Office Action for U.S. Appl. No. 13/234,857, dated Apr. 16, 2015, 17 pgs.
Office Action for U.S. Appl. No. 13/758,585, dated Jun. 10, 2015, 20 pgs.
Office Action for U.S. Appl. No. 13/758,585, dated Oct. 30, 2015, 14 pgs.

SYSTEMS AND METHODS FOR PHLEBOTOMY THROUGH A PERIPHERAL IV CATHETER

CROSS-REFERENCE TO RELATED APPLICATION

This application is a continuation of U.S. patent application Ser. No. 13/234,857 entitled, "Systems and Methods for Phlebotomy Through a Peripheral IV Catheter," filed Sep. 16, 2011, which claims priority under 35 U.S.C. 119(e) to Provisional Patent Application Ser. No. 61/479,223 entitled "Systems and Methods for Phlebotomy Through a Peripheral IV Catheter," filed on Apr. 26, 2011, the disclosures of which are incorporated herein by reference in their entireties.

BACKGROUND

The embodiments described herein relate generally to medical devices. More particularly, the embodiments described herein relate to systems and methods for phlebotomy through an intravenous catheter.

The typical hospitalized patient encounters a needle every time a doctor orders a lab test. The standard procedure for blood extraction involves using a metal needle ("butterfly needle") to "stick" patients' veins in their arms or hands. Blood drawing is a manual, labor-intensive process, with the average patient requiring hours of direct skilled labor during a typical hospital stay. This needle stick is not only painful and a major source of patient dissatisfaction, but the nurses or specialized blood drawing personnel (phlebotomists) often have difficulty finding the vein in approximately 10-15% of patients, resulting in multiple, painful "stick" attempts. This results in significantly higher material and labor costs (needles and tubing must be disposed of after every attempt) and increased patient pain and bruising.

The current process for drawing blood is inefficient, taking on average 7-10 minutes, and more than 21 minutes for 10% of patients. These 10% of patients are referred to as Difficult Intra-Venous Access or more commonly as "tough stick" patients. If superficial veins are not readily apparent, blood can be forced into the vein by massaging the arm from wrist to elbow, tapping the site with the index and middle finger, applying a warm, damp washcloth to the site for 5 minutes, or by lowering the extremity over the bedside to allow the veins to fill. Each of these methods is time consuming and therefore costly.

Peripheral IV catheters (PIVs) are inserted into most patients while they are hospitalized and used for infusing fluids and medications. However, they are not designed for blood extractions. The failure rates for aspiration reach 20-50% when PIVs have been left inserted for more than a day. Blood extracted from PIVs is often hemolyzed, defined as the rupture of red blood cells and the release of their contents into surrounding fluid, resulting in a discarded sample and need to repeat the blood collection.

There are several mechanical barriers that can contribute to the shortcomings of extracting blood from a PIV. First, most catheters are formed from a soft bio-reactive polymer, the use of this material has led to a potential narrowing or collapse of the catheter as the negative pressure is applied for aspiration. Additionally, with longer indwelling times comes an increase in debris (e.g., fibrin/platelet clots) that build up on the tip of the catheter and within the lumen. This explains the relationship between failure rate and indwelling time. A third significant barrier is attributed to a "suction cup" effect, wherein the negative pressure created by aspiration through the catheter and the possible curved path of a vein result in the tip of the catheter adhering to the wall of the vein. As the negative pressure increases the vein can rupture resulting in "blowing the vein", a major concern for phlebotomists during aspiration through a PIV.

Thus, a need exists for an improved system and method for phlebotomy.

SUMMARY

Systems and methods for phlebotomy are described herein. In some embodiments, an apparatus includes an introducer, and a catheter. The catheter includes a proximal end and a distal end defining a lumen. The introducer includes a proximal end and a distal end defining a lumen and is configured to receive the catheter. An actuator, operatively coupled to the catheter, is configured to move the catheter between a first configuration, in which the catheter is substantially within the introducer, and a second configuration, in which the catheter is substantially outside the introducer. A locking mechanism, coupled to the distal end of the introducer, is configured to couple the introducer to a peripheral intravenous line. The catheter extends past an end of the peripheral intravenous line when in the second configuration.

DETAILED DESCRIPTION

Figure 1:
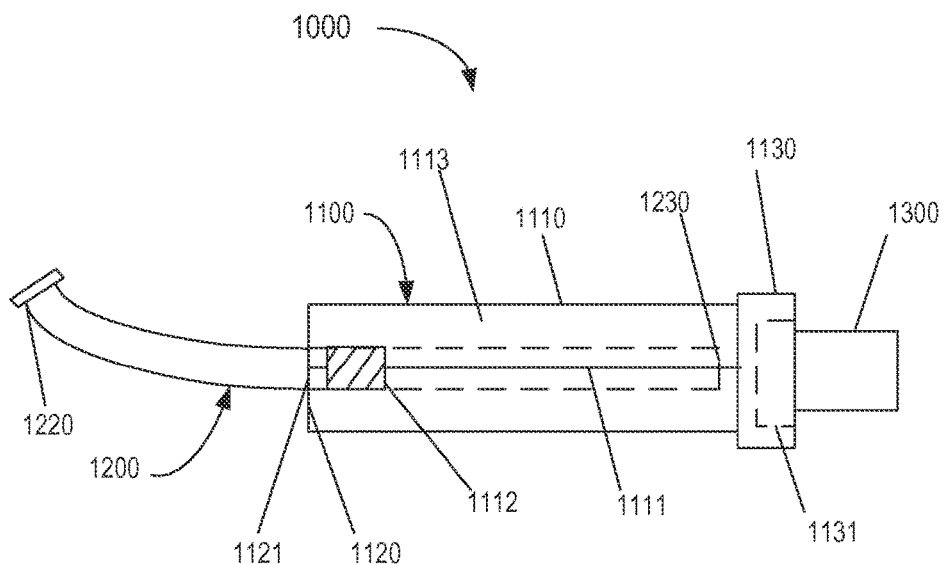
FIG. 1 is a schematic illustration of an apparatus according to an embodiment in a first configuration.

Systems and methods for phlebotomy are described herein. In some embodiments, an apparatus includes an introducer, and a catheter. The catheter includes a proximal end and a distal end defining a lumen. The introducer includes a proximal end and a distal end defining a lumen and is configured to receive the catheter. An actuator, operatively coupled to the catheter, is configured to move the catheter between a first configuration, in which the catheter is substantially within the introducer, and a second configuration, in which the catheter is substantially outside the introducer. A locking mechanism, coupled to the distal end of the introducer, is configured to couple the introducer to a peripheral intravenous line. The catheter extends past an end of the peripheral intravenous line when in the second configuration.

In some embodiments, a method includes coupling an introducer sheath to a peripheral intravenous line (e.g., saline locked device, heparin locked device, or the like), the introducer sheath having a proximal end and a distal end. The method further includes advancing a catheter from a first position inside the introducer sheath and outside the peripheral intravenous line to a second position substantially outside the introducer sheath and inside the peripheral intravenous line. In some embodiments, the catheter has a length greater than a length of the peripheral intravenous line, while in other embodiments, the catheter, in the second position, is shorter than the peripheral intravenous line. A container is then coupled to the proximal end of the introducer sheath, the container being fluidically coupled to the catheter. The catheter is later withdrawn from the second position to the first position.

In some embodiments, a catheter has a proximal end and a distal end and defines a lumen therethrough. An introducer has a proximal end and a distal end and defines a lumen therethrough. The introducer is configured to receive the catheter therein. An adapter is coupled to the introducer. The adapter has a distal end configured to be coupled to a peripheral intravenous line. The adapter defines a first lumen and a second lumen. The first lumen has a first diameter and is configured to receive the catheter therethrough. The second lumen is orthogonal to the first lumen. An actuator is operatively coupled to the catheter and is configured to move the catheter between a first configuration and a second configuration. The catheter extends past the distal end of the adapter in the second configuration.

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the term "stiffness" relates to an object's resistance to deflection, deformation, and/or displacement by an applied force. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

Stiffness is an extensive property of the object being described, and thus is dependent upon the material from which the object is formed as well as certain physical characteristics of the object (e.g., shape and boundary conditions). For example, the stiffness of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be increased, for example, by introducing into the object and/or constructing the object of a material having a high modulus of elasticity.

Similarly, a material's hardness is an intensive property of the constituent material and describes the measure of how resistant the material is to various kinds of permanent shape change when a force is applied. In discussing the hardness and the subsequent effect on the stiffness of a catheter, the Shore durometer scale is generally used. There are several scales for durometers with two commonly used in describing plastics, polymers, elastomers, and/or rubbers, namely, type A and type D, where type A is generally used for softer materials and type D is generally used for harder materials. The Shore durometer of a material is denoted by a number between 0 and 100, with higher numbers indicating a harder material, followed by the type of scale. For instance, a first material can be measured as having a Shore durometer of 40 Shore A and a second material can be measured as having a Shore durometer of 60 Shore D. Therefore, according to the Shore durometer scale, the second material is harder and thus, more stiff than the first material.

Figure 2:
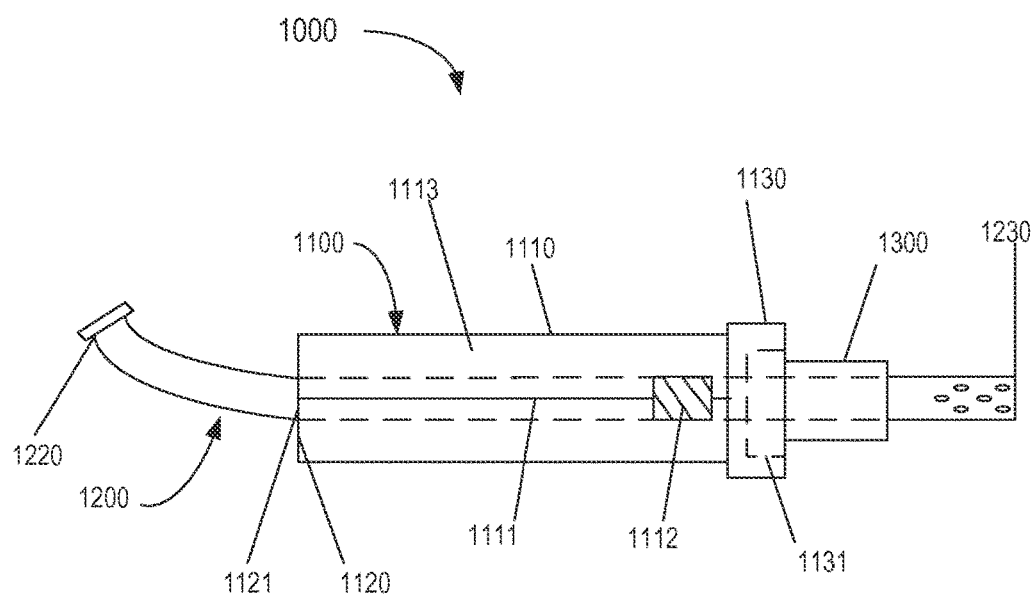
FIG. 2 is a schematic illustration of an apparatus according to an embodiment in a second configuration.

FIG. 1 is a schematic illustration of an apparatus 1000 for phlebotomy through a peripheral intravenous line or catheter in a first configuration according to an embodiment. The apparatus 1000 includes an introducer 1100 and a catheter 1200. The catheter 1200 is movably coupled (e.g., slidably coupled, rotatably coupled, etc.) to the introducer 1100. The introducer 1100 includes a sheath 1110 defining a lumen 1113 between a proximal end 1120 and a distal end 1130 and configured to house, at least partially, the catheter 1200. The proximal end 1120 includes an opening or port 1121, such that the catheter 1200 moves from the first, retracted configuration (FIG. 1) to a second, extended configuration, (FIG. 2). Similarly stated, the port 1121 at the proximal end 1120 of the introducer 1100 is configured such that the catheter 1200 may move through the port 1121 from the first configuration to the second configuration. Moreover, the port 1121 can be any suitable port such as an opening in the proximal end of the introducer 1100 and can include an o-ring, a gasket, or can be a self-sealing port and can be lubricated using any suitable lubrication to aid in the movement and/or sealing of the catheter 1200 therein. The distal end 1130 of the introducer 1100 includes a locking mechanism 1131 configured to fluidically couple a peripheral intravenous line 1300 to the introducer 1100 and place the catheter 2200 into fluid communication with the peripheral intravenous line 1300. The locking mechanism 1131 can be any suitable locking mechanism that creates a fluid-tight seal. In some embodiments, the locking mechanism can be a Luer lock or similar configuration. In some embodiments, the peripheral intravenous line 1300 is in a sealed configuration until the locking mechanism 1131 is coupled to the intravenous line 1300. Once the locking mechanism 1131 is coupled to the intravenous line 1300, the seal can be opened to allow access for the catheter 1200.

FIG. 2 is a schematic illustration of an apparatus 1000 according to an embodiment in a second configuration. The apparatus 1000 includes an introducer 1100 and a catheter 1200. The catheter 1200 defines a lumen 1201 between a proximal end 1220 and a distal end 1230 and may be any suitable diameter and stiffness. In particular, the catheter 1200 is between a 16-gauge and 26-gauge and having a Shore durometer of 20 Shore A to 50 Shore D. Said another way, the catheter 1200 can be any suitable diameter to be inserted through the peripheral intravenous line 1300 and can be sufficiently stiff to be advanced through the peripheral intravenous line 1300. An actuator 1112 is operatively coupled to the catheter 1200 through a groove or slot 1111 in the introducer 1100. The actuator 1112 is configured to move the distal end 1230 of the catheter 1200 from the first configuration, shown in FIG. 1, to the second configuration substantially outside the introducer 1100, as shown in FIG. 2. In the second configuration, the length of the distal end 1230 of the catheter 1200 is greater than the length of the peripheral intravenous line 1300 and the catheter 1200 extends past the distal end of the intravenous line 1300.

In some embodiments, the catheter 1200 can be moved to a third configuration in which it is retracted back into the introducer 1100. The third configuration is substantially similar to the first configuration (FIG. 1) in that the catheter 1200 is positioned in the introducer such that the user does not come into contact with bodily fluids. While in the first configuration and the third configuration, the apparatus 1000 can be disconnected from or connected to a peripheral intravenous line 1300. Said another way, the apparatus 1000 can be in the first configuration before it is coupled to the peripheral intravenous line 1300, then remain in the first configuration for a period of time after being coupled to the peripheral intravenous line 1300. Similarly, the apparatus 1000 can be moved to the third configuration, can be disconnected from the peripheral intravenous line 1300, and then remain in the third configuration.

Figure 3:
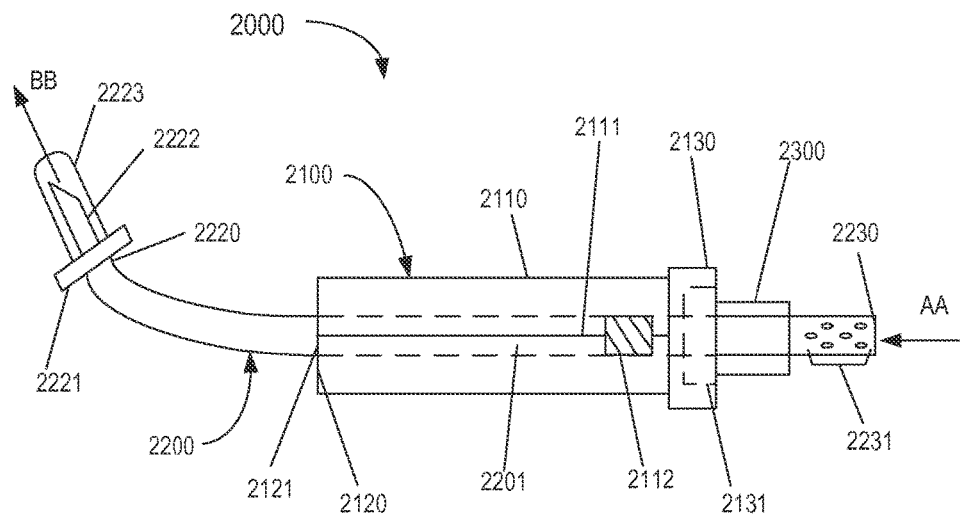
FIG. 3 is a detailed schematic illustration of an apparatus according to an embodiment in a second configuration.

FIG. 3 is a detailed schematic illustration of an apparatus 2000 according to an embodiment in a second configuration. The apparatus 2000 includes an introducer 2100 and a catheter 2200. The catheter 2200 includes a distal end 2230 and a proximal end 2220. The distal end 2230 of the catheter 2200 includes a set of openings 2231 such that when in the second configuration (i.e., when the distal end 2230 of the catheter 2200 is in the vein and outside the intravenous line) the openings 2231 act to transport a bodily fluid (i.e., blood) to a volume outside the catheter 2200. The set of openings can be of any arrangement on the circumference of the catheter 2200 and can include the end of the catheter 2200. Similarly stated, the catheter 2200 having the distal end 2230 can be substantially open at the tip surface. Each opening 2231 can be of any suitable shape or size and are not necessarily similar to any other opening included in the set of openings. In some embodiments, the catheter 2200 defines a single opening.

The proximal end 2220 of the catheter 2200 is fluidically coupled to a locking mechanism 2221, as shown in FIG. 3. The locking mechanism 2221 can be any suitable locking mechanism such as a Luer lock or the like. A needle 2222 is fluidically coupled to the locking mechanism and at least partially disposed within a sheath 2223. The sheath 2223 can be any material with a suitable flexibility and/or compressibility such that the needle 2222 can extend through the sheath 2223 when engaged with a conventional phlebotomy fluid container (e.g., a Vacutainer®). The locking mechanism 2221 is configured to couple to a suitable fluid containment system such as a Vacutainer® holder (not shown in FIG. 3) and place the needle 2222 in fluid communication with the fluid containment system. The sheath 2223 is configured to compress when the locking mechanism 2221 is coupled to the fluid containment system. This arrangement facilitates the passage of bodily fluids through the set of openings 2231 of the catheter 2200, as shown in FIG. 3 by arrow AA, through the catheter 2200, and exiting the catheter 2200 through the needle 2222, as shown in FIG. 3 by arrow BB.

Figure 4:
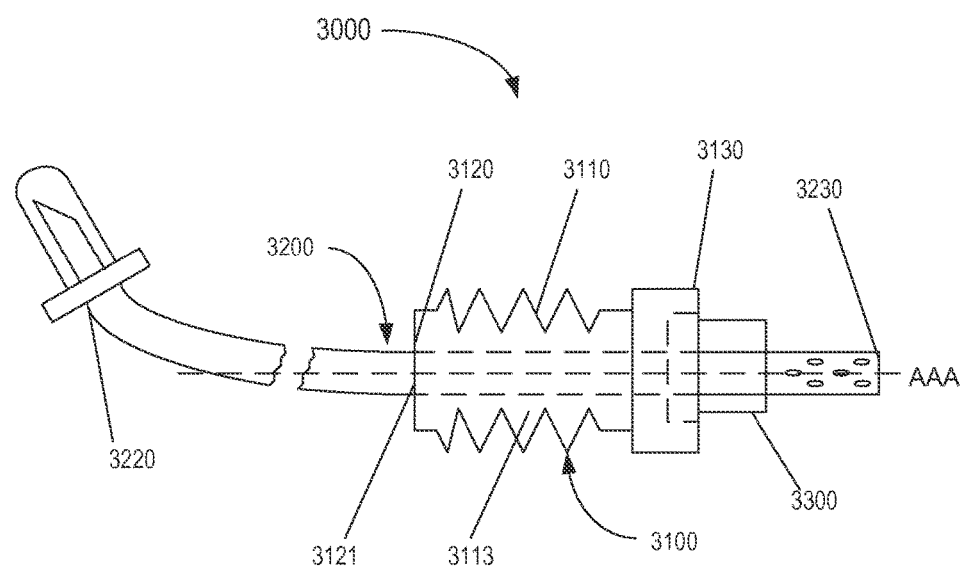
FIG. 4 is a schematic illustration of an apparatus according to an embodiment in a second configuration.

FIG. 4 is a schematic illustration of an apparatus 3000 for phlebotomy through a peripheral intravenous catheter in a second configuration according to an embodiment. The apparatus 3000 includes an introducer 3100 and a catheter 3200. The introducer 3100 includes a sheath 3110 defining a lumen 3113 between a proximal end 3120 and a distal end 3130 and configured to house, at least partially, the catheter 3200. The distal end 3130 of the introducer 3100 includes a locking mechanism 3131 configured to fluidically couple the introducer 3100 to a peripheral intravenous line 3300 and place the catheter 3200 into fluid communication with the peripheral intravenous line 3300. The locking mechanism 3131 can be any suitable locking mechanism that creates a fluid-tight seal. In some embodiments, the locking mechanism can be a Luer lock or similar configuration. The sheath 3110, having a given stiffness, is such that when applying a force to the proximal end 3120, the sheath 3110 compresses along an axis AAA, advancing the catheter 3200 to the second configuration. Said another way, as the sheath 3110 of the introducer 3100 is compressed, the catheter 3200 moves from the first configuration (FIG. 1) to a second configuration substantially outside the introducer 3100, as shown in FIG. 4. Furthermore, the stiffness of the sheath 3110 is an extensive property and as such can have a set of properties (i.e. material, thickness, shape and/or the like) to allow the sheath 3110 to compress along the axis AAA with the desired amount of force applied at the proximal end 3120 of the introducer 3100. The set of properties allow the sheath 3110 to elastically deform (i.e. non-permanently) such that when the force is no longer applied to the proximal end 3120 of the introducer 3100, the apparatus 3000 returns to the first configuration. In the second configuration, the distal end 3230 of the catheter 3200 extends past the distal end of the peripheral intravenous line 3300. This arrangement allows for the transport of a bodily fluid to a volume outside the catheter 3200 and when complete, the apparatus 3000 returns to a third configuration, which is substantially the same as the first configuration.

Figure 5:
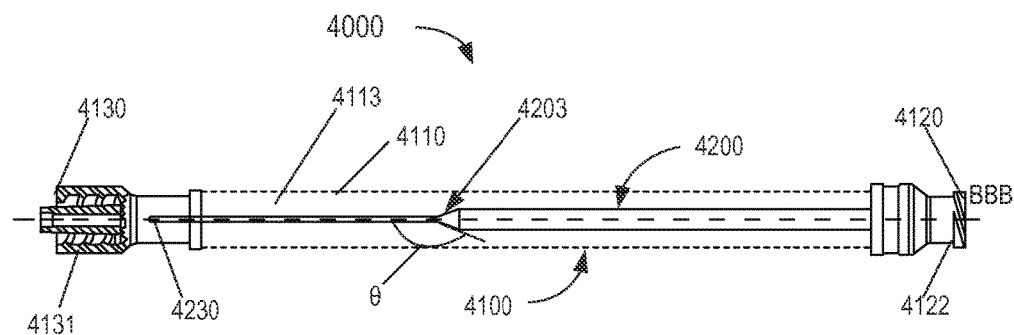
FIG. 5 is a side view of an apparatus according to an embodiment in a first configuration.

FIG. 5 is a side view of an apparatus 4000 according to an embodiment in a first configuration. The apparatus 4000 includes an introducer 4100 and a catheter 4200. The introducer 4100 includes a sheath 4110 defining a lumen 4113 between a proximal end 4120 and a distal end 4130 and configured to house, at least partially, the catheter 4200. Although shown in FIG. 5 as being cylindrical, the introducer 4100 can be any suitable shape. Moreover, the lumen 4113, defined by the interior walls of the sheath 4110 is not necessarily the same shape as the exterior walls of the sheath 4110. Said a different way, the interior and exterior walls of the sheath 4110 can have a different cross sectional shape. The proximal end 4120 of the introducer 4100 is coupled to a locking mechanism 4122. The locking mechanism 4122 can be any suitable locking mechanism such as a Luer lock or the like. The locking mechanism 4122 is configured to couple to a suitable fluid containment system such as a Vacutainer® holder (not shown in FIG. 5) and place the catheter 4200 in fluid communication with the fluid containment system.

The distal end 4130 of the introducer 4100 includes a locking mechanism 4131 configured to fluidically couple a peripheral intravenous line (not shown in FIG. 5) to the introducer 4100 and place the catheter 4200 into fluid communication with the peripheral intravenous line. The locking mechanism 4131 can be any suitable locking mechanism that creates a fluid-tight seal. In some embodiments, the locking mechanism 4131 is in a sealed configuration until the locking mechanism 4131 is coupled to the intravenous line. Once the locking mechanism 4131 is coupled to the intravenous line, the seal can be opened to allow access for the catheter 4200. In addition, while in the unlocked configuration, the locking mechanism 4131 of the distal end 4130 and the locking mechanism 4122 of the proximal end 4120 create an isolated housing for the catheter 4200 therein. Stated similarly, prior to the proximal end locking mechanism 4122 and distal end locking mechanism 4131 being unlocked and before the catheter 4200 is in the second configuration, the catheter 4200 is sterile. Furthermore, the catheter 4200, when in the second configuration and having contacted the desired bodily fluid, can be moved to the third configuration (i.e., returned to the first configuration) thereby isolating the used distal end 4230.

Figure 6:
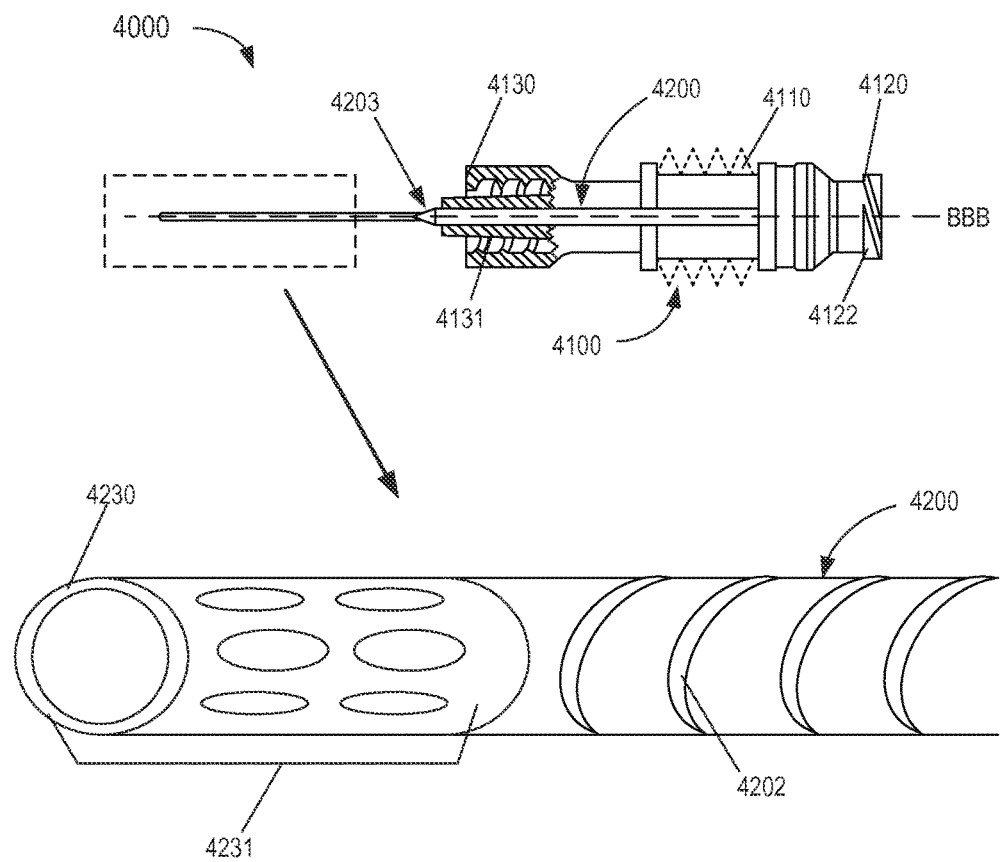
FIG. 6 is a cross-sectional view of a portion of an apparatus according to an embodiment.

The sheath 4110 has a given stiffness such that when a force is applied to the proximal end 4120 the sheath 4110 compresses along an axis BBB advancing the catheter 4200 to a second configuration (FIG. 6). Said another way, as the sheath 4110 of the introducer 4100 is compressed, the catheter 4200 moves from the first configuration to the second configuration substantially outside the introducer 4100 (i.e., the sheath 4110 retracts). The properties of the sheath 4110 can be any set of properties discussed herein such that applying a desired amount of force to proximal end 4120 allows the sheath to compress along axis BBB. In the second configuration, the distal end 4230 of the catheter 4200 extends past the distal end of the peripheral intravenous line and allows for the transport of a bodily fluid to a volume outside of the catheter 4200.

The catheter 4200 includes a distal end 4230 and tapered portion 4203. The tapered portion is such that the diameter of the catheter 4200 is reduced at a given location, as shown in FIG. 5. The taper angle θ can be any suitable angle such that the catheter 4200 is allowed to advance fully to the second configuration (FIG. 6). Moreover, the taper angle θ is such that a laminar flow (i.e., smooth layered flow) is achieved. In some embodiments, the catheter 4200 can include a stiffening wire 4202, as shown in the magnified portion of FIG. 6, and can be configured to coil around the walls of the catheter 4200 providing the catheter 4200 with a desired stiffness. Moreover, the stiffening wire 4202, being coiled around the catheter 4200, can provide the flexibility to advance through a set of walls defining a lumen (i.e., veins, arteries, peripheral intravenous line, and/or the like) without kinking or binding. In addition, the stiffening wire 4202 can provide the catheter 4200 with enough stiffness to facilitate its advancement through the lumen.

The distal end 4230 of the catheter 4200 includes a set of openings 4231 such that when in the second configuration (i.e., when the distal end 4230 of the catheter 4200 is in the vein and outside the intravenous line) the openings 4231 act to transport a bodily fluid (i.e., blood) to a volume outside the catheter 4200. The set of openings 4231 can be of any arrangement on the circumference of the catheter 4200 and can include the end of the catheter 4200. Similarly stated, the catheter 4200 having the distal end 4230 can be substantially open at the tip surface. Although FIG. 6 shows the distal end 4230 of the catheter 4200 as substantially flat, the distal end 4230 may be any suitable shape, (e.g. conical or spherical) and can have any suitable degree of rounded edges. Each opening 4231 can be of any suitable shape or size and are not necessarily similar to any other opening 4231 included in the set of openings 4231. The arrangement of the set of openings 4231 is configured to introduce a laminar flow through catheter 4200 to a volume substantially outside the catheter 4200 and thus avoid hemolysis.

In some embodiments, a blood collection system consists of two elements: (1) the introducer/catheter blood collection assembly described above; and (2) a y-adapter that is configured to attach to a standard 16 g or 22 g peripheral IV catheter. The y-adapter includes a dedicated port for the blood collection device and another standard port for conventional medicine and fluid infusion.

Figure 7:
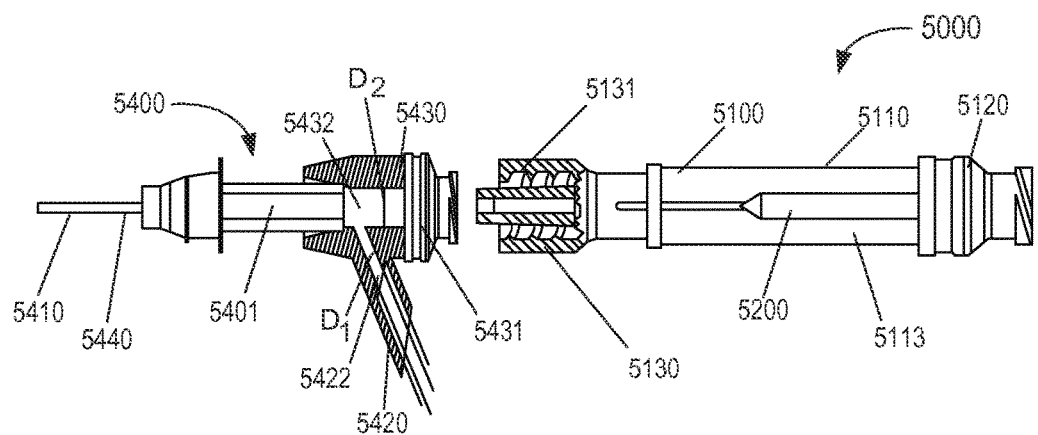
FIG. 7 is a side view of an apparatus according to an embodiment in a first configuration.

FIG. 7 is a cross-sectional view of y-adapter 5400 and an apparatus 5000 in a first configuration according to an embodiment. The apparatus includes an introducer 5100 and a catheter 5200. The introducer 5100 includes a sheath 5110 defining a lumen 5113 between a proximal end 5120 and a distal end 5130 and configured to house, at least partially, the catheter 5200. In some embodiments, the y-adapter 5400 is configured to be coupled between the introducer 5100 and intravenous line (not shown in FIG. 7). The y-adapter includes a distal end 5410 and defines two distinct ports. A first port 5420 of the y-adapter 5400 defines a first lumen 5422 with a first diameter $D_1$. The first port 5420 is configured such that the first port 5420 is substantially similar in size, shape, configuration, and functionality of a conventional y-adapter. Moreover, the first port 5420 is configured such that the backflow of a bodily fluid cannot exit the first port 5420. More specifically, the first lumen 5422 defined by the walls of the first port 5420 can be such that the lumen 5422 restricts the backflow of a bodily fluid (i.e. blood). In some embodiments, the backflow can be prevented using a valve, screw cap, flip cap, port, and/or the like. A second port 5430 of the y-adapter 5400 defines a second lumen 5432 with a second diameter $D_2$. The second diameter $D_2$ can be larger than the first diameter $D_1$, as shown in FIG. 7, in some embodiments, the second diameter $D_2$ can be similar or smaller than the first diameter $D_1$. More particularly, the diameter $D_2$ of the second port 5430 is large enough to accept up to, for example, an 18-gauge catheter. The y-adapter can be of any suitable material and/or be of similar material to that of a conventional y-adapter.

The first lumen 5422 defined by the first port 5420 and the second lumen 5432 defined by the second port 5430 converge to a common lumen 5401 before the distal end 5410 of the y-adapter 5400, as shown in FIG. 7. The second port 5420 is configured such that the second lumen 5432 is substantially coaxial with the common lumen 5401 and has a diameter substantially the same as the diameter $D_2$. In some embodiments, the walls that define the common lumen 5401 and the walls that define the second lumen 5432 are similar. The second port 5430 is fluidically coupled to a locking mechanism 5431 configured to couple the y-adapter to the introducer 5100. The locking mechanism 5431 can be a Luer lock or the like. In some embodiments, the y-adapter 5400 is in a sealed configuration until coupled to the locking mechanism 5131 at the distal end 5130 of the introducer 5100. Once the locking mechanism 5431 is coupled to the introducer 5100, the seal can be opened to allow access for the catheter 5200 to advance to a second configuration, shown in FIG. 8 (note the introducer is not shown coupled to the y-adapter in FIG. 8).

In some embodiments, the distal end 5410 of the y-adapter 5400 is coupled to a peripheral intravenous line 5440 such as, for example, a conventional peripheral intravenous line. In some embodiments, the y-adapter 5400 is monolithically formed with the peripheral intravenous line 5440. In some embodiments, the distal end 5410 of the y-adapter 5400 can be coupled to a peripheral intravenous line using any suitable locking mechanism. Similarly, the second port 5420 of the locking mechanism 5431 configured to couple the y-adapter 5400 to the introducer 5100 can monolithically formed with the introducer 5100. Said another way, in some embodiments, a separate introducer is not required, but rather a portion of the y-adapter can serve as the introducer.

Figure 8:
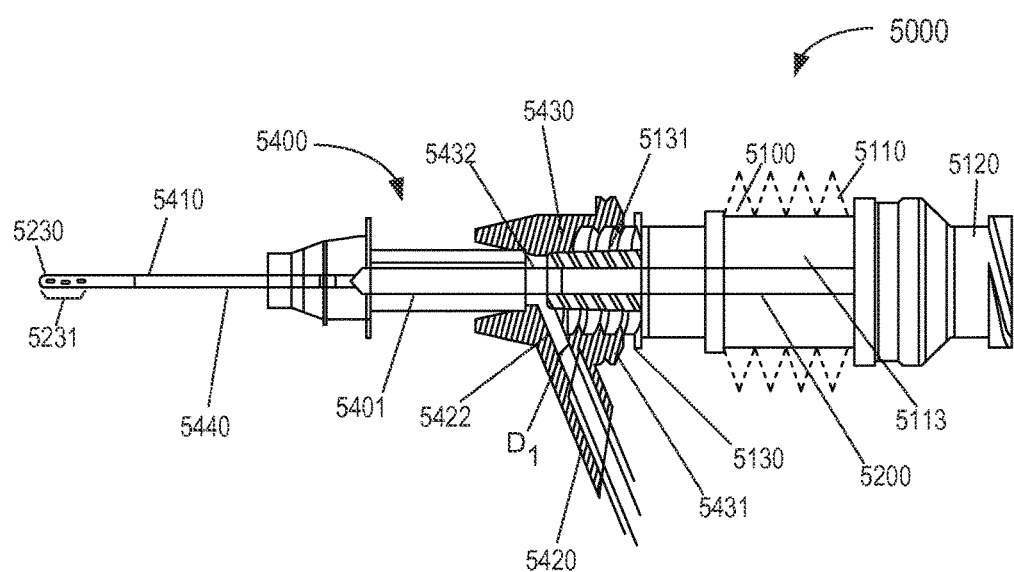
FIG. 8 is a side view of an apparatus according to an embodiment in a second configuration.

As shown in FIG. 8, the distal end 5230 of the catheter 5200 in the second configuration is advanced substantially past the peripheral intravenous line 5440. The distal end 5230 of the catheter 5200 includes a set of openings 5231 such that when in the second configuration (i.e., when the distal end 5230 of the catheter 5200 is in the vein and outside the intravenous line) the openings 5231 act to transport a bodily fluid (i.e., blood) to a volume outside the catheter 5200. The set of openings can be of any arrangement on the circumference of the catheter 5200 and can include the end of the catheter 5200. Similarly stated, the catheter 5200 having the distal end 5230 can be substantially open at the tip surface. Each opening 5231 can be of any suitable shape or size and are not necessarily similar to any other opening included in the set of openings. The catheter 5200, in the second configuration and having transported the desired bodily fluid, can be returned to the third configuration (i.e., the first configuration) (FIG. 7) thereby isolating the used distal end 5230.

Figure 9A:
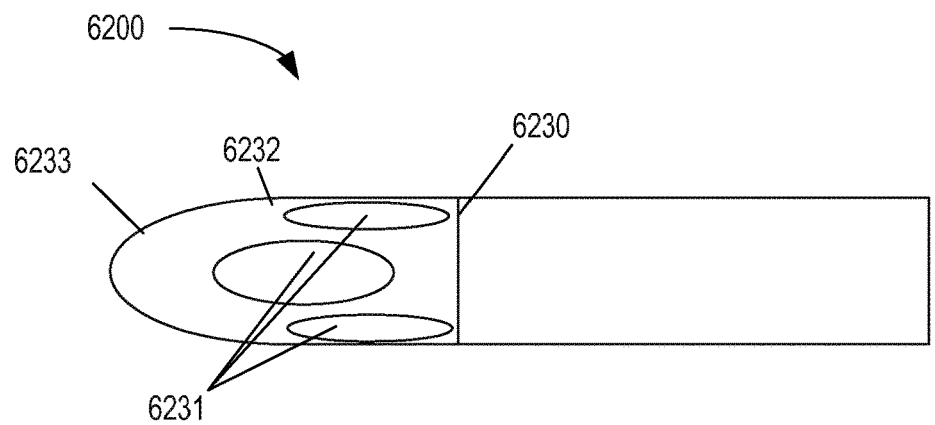
FIGS. 9A and 9B are side views of an apparatus according to embodiments.
Figure 9B:
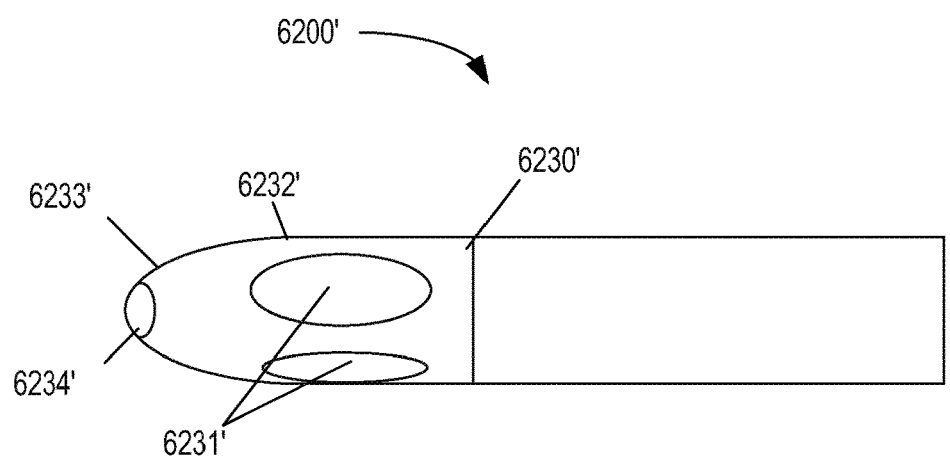

While catheters are described herein as including a distal end of a particular configuration (i.e., with circumferential openings, etc.), in some embodiments the distal end of the catheter can include a different structure configured to facilitate the drawing of blood through the catheter. For example, FIG. 9A illustrates a catheter 6200 that includes a distal end 6230 with a bullet-shaped tip 6232. The bullet-shaped tip 6232 includes an end portion 6233 configured to be a substantially closed rounded tip and, as such, can be used to move through clots existing within a peripheral intravenous line. The bullet-shaped tip 6232 includes a set of side-wall openings 6231 that are operative to transport a bodily fluid (i.e., blood) to a volume outside the catheter 6200. In some embodiments, such as, for example, a catheter 6200' shown in FIG. 9B, a bullet-shaped tip 6232' includes an end portion 6233' that defines an end opening 6234'. In such embodiments, the bullet-shaped tip 6232' includes a set of side-wall openings 6231'. The end opening 6234' and the side openings 6231' can be configured to produce a laminar flow and act to transport a bodily fluid (i.e., blood) to a volume outside the catheter 6200'. While the openings 6231, 6231' are illustrated as having a particular configuration, the shape and orientation/relative position of the openings can be varied to facilitate the fluid flow through the catheter.

Figure 10A:
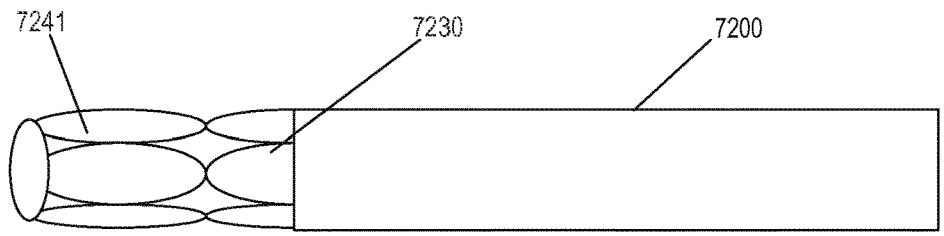
FIGS. 10A-10C are side views of an apparatus according to embodiments.
Figure 10B:
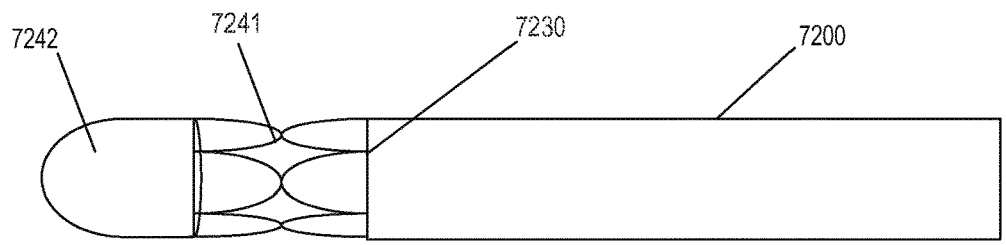
Figure 10C:
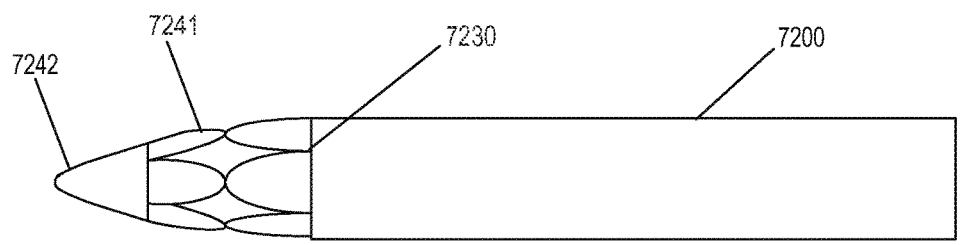

In some embodiments, for example those shown in FIGS. 10A-10C, a catheter 7200 includes a distal end 7230 with a wireframe tip 7241 having a stent-like configuration. The wireframe tip 7241 can be a flexible mesh configured to extend away from the distal end 7230 of the catheter 7200. The wireframe tip 7241 can act to transport a bodily flow (i.e., blood) to a volume outside the catheter 7200. In some embodiments, the wireframe tip 7241 can include a capped end 7242. The capped end 7242 can be any suitable size, shape, or configuration and, in some embodiments, can include any suitable number of openings.

Figure 11A:
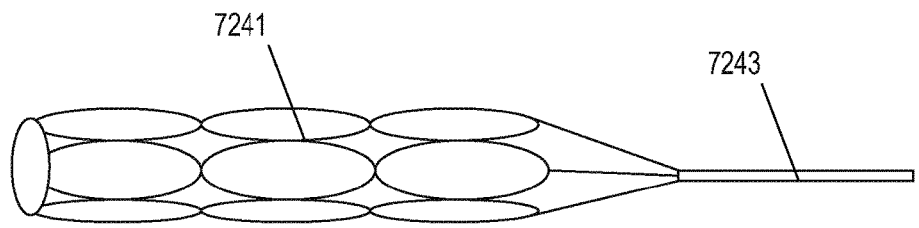
FIGS. 11A-11C are side views of an apparatus according to embodiments.
Figure 11B:
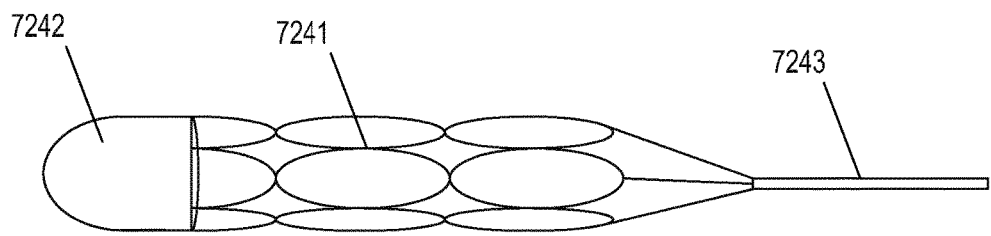
Figure 11C:
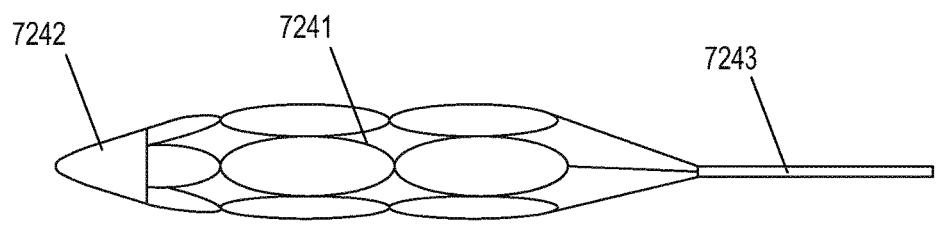

In some embodiments, the wireframe tip 7241 can be connected to a guide wire 7243 and used without an additional catheter, as shown in FIGS. 11A-11C. Similarly stated, the wireframe tip 7241 can be inserted into an existing peripheral intravenous line via a guide wire and without the catheter of FIG. 10. In this manner, the wireframe tip 7241 can act as a stent and support the walls of the vein such that blood can be drawn through the existing peripheral intravenous line. In such a configuration, the wireframe tip 7241 can be positioned within the existing peripheral intravenous line at any suitable location. For example, the wireframe tip can be positioned adjacent the distal end of the intravenous line.

The components of the blood draw apparatus and the y-Adapter can be packaged together or separately. The y-adapter can also be sold in a package with other IV dressing materials. In some embodiments, the y-adapter can remain on the IV as long as the IV is in the patient.

The blood draw apparatus can be used with a variety of peripheral IVs. The apparatus allows efficient blood draw while still maintaining the integrity of the sample. In some embodiments, for example, the apparatus will facilitate 20 ml of blood to be drawn in approximately 1-2 minutes. While extracting blood, the blood flow can be laminar to avoid turbulence in the catheter to minimize hemolysis.

While the blood draw apparatus can be used in a variety of settings (ER, in-patient, etc.), two examples of scenarios are described herein. In the first scenario, the patient has a single peripheral IV. In the second scenario, which is typically less common, the patient has a dedicated second peripheral IV just for phlebotomy purposes. Only one y-adapter is required per patient, and can be attached for the life of the IV, for example, which is typically 3-4 days. A new catheter can be used for each blood draw.

The assembly of the blood draw apparatus can be the same in either scenario. First, the apparatus is coupled to the y-adapter. Second, the catheter is advanced through the y-adapter and pushed through the peripheral IV catheter into the patient's vein. Once in the vein, a syringe or a negative pressure collection container/tube (e.g., a Vacutainer® tube) is connected to the rear port and fluidically coupled to the catheter to draw and store blood.

The following scenario is provided by way of example. The nurse or phlebotomist inserts a peripheral IV into a patient's arm. The peripheral IV is inserted following standard guidelines and the y-adapter is attached. When it is time to draw blood, the provider can turn off the IV, if it is on, for approximately 1-5 minutes to allow medicine or IV fluids to disperse from the blood-drawing site. To draw the blood sample, the provider attaches the blood draw apparatus to the blood draw port on the y-adapter, advances the internal catheter through the peripheral IV and into the vein. Next, the provider can attach the negative pressure collection container(s)/tube(s) to the apparatus (i.e., place the tube in fluid communication with the blood draw apparatus) to extract the blood sample. In use, a user can discard, for example, the first 3-6 ml of the fluid or blood sample as "waste" then using the next tube(s) as the intended sample. This "wasting" procedure ensures all of the dead space fluid, like saline or medications, are cleared from the vein, peripheral IV and y-adapter as to not contaminate the testing sample being drawn.

In the scenario in which there is a dedicated peripheral IV line for blood draw purposes, the provider inserts a peripheral IV into one arm to administer medicine and another peripheral IV into the opposite arm specifically for blood drawing purposes. When it is time to draw blood, the provider simply follows the steps mentioned above and there is no need to wait the 2-3 minutes to allow fluid or medicine dispersal as in the first scenario.

Each of the components discussed herein can be monolithically constructed or can be a combination of parts. For example, in reference to FIG. 7, the y-adapter 5400 and the introducer 5100 are coupled using locking mechanisms 5431 and 5131, respectively. The y-adapter 5400 and the introducer 5100 can be the same component, wherein the y-adapter is an integral part of the introducer 5100 and vice-versa. Other aspects of the apparatus shown and described can be modified to affect the performance of the apparatus. For example, the openings in the set of openings described herein at the distal end of the catheter can be in any arrangement, size shape, and/or number, to create preferable flow conditions through the catheter.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. While various embodiments have been described as having particular features and/or combinations of components, other embodiments are possible having a combination of any features and/or components from any of embodiments as discussed above.

What is claimed is:

1. An apparatus, comprising:
a catheter having a proximal end portion and a distal end portion and defining a lumen extending through the proximal end portion and the distal end portion;
an introducer having a proximal end portion and a distal end portion and defining a lumen extending through the proximal end portion of the introducer and the distal end portion of the introducer, the lumen of the introducer configured to receive the catheter, the distal end portion of the introducer configured to be coupled to an indwelling peripheral intravenous line; and
an actuator coupled to the introducer, a portion of the actuator being movably disposed within the introducer and coupled to the proximal end portion of the catheter, the actuator configured to move relative to the introducer to move the catheter between a first position and a second position, the catheter disposed within the introducer when in the first position, the distal end portion of the catheter disposed beyond the distal end portion of the introducer such that at least a portion of the catheter is disposed within the indwelling peripheral intravenous line when the catheter is in the second position and the introducer is coupled to the indwelling peripheral intravenous line, the introducer having a fixed length as the actuator moves the catheter between the first position and the second position.

2. The apparatus of claim 1, further comprising:
an adapter coupled between the introducer and the indwelling peripheral intravenous line, the adapter configured to selectively place the introducer in fluid communication with the indwelling peripheral intravenous line.

3. The apparatus of claim 1, further comprising:
an adapter coupled between the introducer and the indwelling peripheral intravenous line, the adapter configured to selectively place the introducer in fluid communication with the indwelling peripheral intravenous line,
the adapter coupled to a seal configured to selectively control fluid flow through a lumen defined by the adapter.

4. The apparatus of claim 1, wherein the portion of the actuator movably disposed in the introducer is a first portion of the actuator, the actuator including a second portion, the actuator configured to move relative to the introducer in response to a force exerted on the second portion of the actuator.

5. The apparatus of claim 1, wherein the catheter is in the first position when the actuator is in a first actuator position along a length of the introducer, the catheter being moved to the second position as the actuator is moved along the length of the introducer from the first actuator position to a second actuator position along the length of the introducer.

6. The apparatus of claim 1, further comprising:
a port coupled to the proximal end portion of the introducer, the port being in fluid communication with the catheter, the port configured to place the lumen of the catheter in fluid communication with a volume outside the introducer.

7. The apparatus of claim 1, further comprising one of a sheathed needle, a locking mechanism, a syringe, or an access port coupled to the proximal end portion of the catheter.

8. The apparatus of claim 1, wherein the catheter includes a first material portion having a first stiffness and a second material portion having a second stiffness greater than the first stiffness.

9. The apparatus of claim 1, wherein the catheter has a Shore durometer of approximately 20 Shore A to approximately 50 Shore D.

10. The apparatus of claim 1, wherein the catheter is maintained entirely within the introducer when the catheter is in the first position.

11. An apparatus, comprising:
a catheter having a proximal end portion and a distal end portion and defining a lumen extending through the proximal end portion and the distal end portion;
an introducer having a proximal end portion and a distal end portion, the introducer defining a lumen extending through the proximal end portion of the introducer and the distal end portion of the introducer and configured to receive the catheter, the distal end portion of the introducer configured to be coupled to an indwelling peripheral intravenous line, the introducer defining a slot along a predetermined length of the introducer; and
an actuator coupled to the catheter, a portion of the actuator disposed within the slot defined by the introducer and movable within the slot along the predetermined length of the introducer from a first position to a second position, the catheter being disposed within the introducer when the actuator is in the first position, at least a portion of the catheter being disposed distal to the introducer when the actuator is in the second position such that, when the introducer is coupled to the indwelling peripheral intravenous line, the distal end portion of the catheter extends beyond a distal end portion of the indwelling peripheral intravenous line.

12. The apparatus of claim 11, wherein the introducer is one of integrally coupled or removably coupled to an adapter, the adapter configured to couple the introducer to the indwelling peripheral intravenous line.

13. The apparatus of claim 11, wherein the proximal end portion of the catheter is configured to be coupled to a fluid collection device.

14. The apparatus of claim 11, wherein the distal end portion of the introducer includes a locking mechanism, the locking mechanism configured to couple the introducer to the indwelling peripheral intravenous line.

15. The apparatus of claim 11, wherein the introducer has a fixed length defined between the proximal end portion of the introducer and the distal end portion of the introducer, the predetermined length being along the fixed length of the introducer.

16. An apparatus, comprising:
a catheter having a proximal end portion and a distal end portion and defining a lumen extending through the proximal end portion and the distal end portion;

an introducer having a proximal end portion and a distal end portion, the introducer defining a lumen extending through the proximal end portion of the introducer and the distal end portion of the introducer and configured to receive the catheter;

a locking mechanism coupled to the distal end portion of the introducer and configured to physically and fluidically couple the introducer to an indwelling peripheral intravenous line; and an actuator coupled to the introducer, a portion of the actuator being movably disposed within the introducer and coupled to the proximal end portion of the catheter, the actuator configured to move relative to the introducer to move the catheter between a first position and a second position, the locking mechanism configured to fluidically isolate the catheter within the introducer when the catheter is in the first position, the locking mechanism configured to receive a portion of the catheter as the catheter is moved toward the second position, the distal end portion of the catheter disposed beyond a distal end of the indwelling peripheral intravenous line when the catheter is in the second position and the locking mechanism is coupled to the indwelling peripheral intravenous line, the introducer having a fixed length as the actuator moves the catheter between the first position and the second position.

17. The apparatus of claim 16, wherein the locking mechanism is transitioned from a first configuration, in which at least a portion of a lumen defined by the locking mechanism is substantially sealed to a second configuration, in which the lumen defined by the locking mechanism is substantially unsealed, when the locking mechanism is coupled to the indwelling peripheral intravenous line, a portion of the catheter extending through the lumen of the locking mechanism when the locking mechanism is in the second configuration and the catheter is moved to the second position.

18. The apparatus of claim 16, wherein the locking mechanism is configured to be coupled to an adapter, the adapter configured to be coupled between the locking mechanism and the indwelling peripheral intravenous line, the adapter defining at least one lumen, the catheter configured to extend through the at least one lumen of the adapter when the catheter is in the second position.

19. The apparatus of claim 16, wherein the catheter is in the first position when the actuator is disposed in a first actuator position along a predetermined length of the introducer, the catheter being moved to the second position as the actuator is moved along the predetermined length of the introducer from the first actuator position to a second actuator position, the predetermined length being along the fixed length of the introducer defined between the proximal end portion of the introducer and the distal end portion of the introducer.

20. The apparatus of claim 16, further comprising:
a port coupled to the proximal end portion of the catheter, the port being at least one of a sheathed needle, a locking mechanism, a syringe, or an access port.

* * * * *